US012121367B2

(12) United States Patent
Sakkalis et al.

(10) Patent No.: US 12,121,367 B2
(45) Date of Patent: Oct. 22, 2024

(54) WRIST-WATCH BACK CASES, SYSTEMS AND METHODS FOR MEASURING BIOMARKERS

(71) Applicant: TRAQBEAT TECHNOLOGIES PRIVATE COMPANY, Heraklion Crete (GR)

(72) Inventors: Vangelis Sakkalis, Athens (GR); Matthaios Pediaditis, Heraklion (GR); Emmanouil Georgios Spanakis, Heraklion (GR); Giannis Zacharakis, Heraklion (GR)

(73) Assignee: TRAQBEAT TECHNOLOGIES PRIVATE COMPANY, Heraklion Crete (GR)

( * ) Notice: Subject to any disclaimer, the term of this patent is extended or adjusted under 35 U.S.C. 154(b) by 1017 days.

(21) Appl. No.: 16/979,216

(22) PCT Filed: Mar. 11, 2019

(86) PCT No.: PCT/EP2019/056059
§ 371 (c)(1),
(2) Date: Sep. 9, 2020

(87) PCT Pub. No.: WO2019/175122
PCT Pub. Date: Sep. 19, 2019

(65) Prior Publication Data
US 2020/0405233 A1    Dec. 31, 2020

Related U.S. Application Data

(60) Provisional application No. 62/641,299, filed on Mar. 10, 2018.

(51) Int. Cl.
*A61B 5/00* (2006.01)
*A44C 5/14* (2006.01)
(Continued)

(52) U.S. Cl.
CPC .............. *A61B 5/681* (2013.01); *A44C 5/14* (2013.01); *A61B 5/02427* (2013.01);
(Continued)

(58) Field of Classification Search
CPC . A61B 5/681; A61B 5/02427; A61B 5/02438; A61B 5/7203; A61B 5/02433;
(Continued)

(56) References Cited

U.S. PATENT DOCUMENTS

| 2003/0031524 A1* | 2/2003 | Brunet | B61D 45/001 |
| | | | 410/100 |
| 2015/0173616 A1* | 6/2015 | Zajac | H04Q 9/00 |
| | | | 340/870.07 |

(Continued)

FOREIGN PATENT DOCUMENTS

| CN | 102983848 | * | 9/2015 |
| CN | 106725411 | * | 5/2017 |

(Continued)

OTHER PUBLICATIONS

APM Korea (Photoplethysmography: Second Derivative Photoplethysmography Implementation, Jun. 12, 2013; APMKorea; http://apmkr.com/bio-device/Second_Derivative_Photoplethysmography_Implementation.pdf). (Year: 2013).*

(Continued)

*Primary Examiner* — Alexei Bykhovski
(74) *Attorney, Agent, or Firm* — DP IP GROUP; Franco S. De Liguori

(57) ABSTRACT

A wrist-watch back case for replacing existing back case of a timekeeping device or to be attached thereto is provided. The back case comprises a casing comprising a bottom wall and a side wall thereby defining an inner empty space, at least five openings at the bottom wall, an optoelectronic board, at least two paired radiation sources and at least one (Continued)

radiation detector. Methods for measuring biomarkers, systems and a watchband are also provided.

20 Claims, 10 Drawing Sheets

(51) Int. Cl.
    *A61B 5/024*     (2006.01)
    *G04G 21/02*     (2010.01)

(52) U.S. Cl.
    CPC ........ *A61B 5/02438* (2013.01); *A61B 5/7203* (2013.01); *G04G 21/025* (2013.01); *A61B 5/02433* (2013.01); *A61B 5/725* (2013.01)

(58) Field of Classification Search
    CPC ............ A61B 5/725; A61B 2560/0443; A61B 5/02416; A44C 5/14; G04G 21/025
    See application file for complete search history.

(56) References Cited

U.S. PATENT DOCUMENTS

| | | | |
|---|---|---|---|
| 2016/0103985 A1* | 4/2016 | Shim ..................... | G06F 21/316 726/19 |
| 2016/0357386 A1* | 12/2016 | Choi ...................... | G06V 40/10 |
| 2017/0209055 A1* | 7/2017 | Pantelopoulos ... | A61B 5/02438 |
| 2017/0281081 A1* | 10/2017 | Nousiainen ........ | A61B 5/02438 |
| 2017/0311825 A1* | 11/2017 | Weekly ................ | A61B 5/6815 |

FOREIGN PATENT DOCUMENTS

| | | | |
|---|---|---|---|
| EP | 3117762 | * | 1/2017 |
| WO | WO 2009024273 | * | 2/2009 |

OTHER PUBLICATIONS

Shao et al., Motion Artifact Detection and Reduction in PPG Signals Based on Statistics Analysis, 2017 29th CCDC, IEEE, May 28, 2017, pp. 3114-3119. (Year: 2017).*

Hanyu Shao et al., "Motion Artifact Detection and Reduction in PPG Signals Based on Statistics Analysis", 2017 29th CCDC, IEEE, May 28, 2017, pp. 3114-3119.

Meir Nitzan et al., "Pulse Oximetry: Fundamentals and Technology Update", Medical Devices: Evidence and Research, Jul. 1, 2014, p. 231.

Photoplethysmography: "Second Derivative Photoplethysmography Implementation", Jun. 12, 2013.

* cited by examiner

WRIST-WATCH BACK CASES, SYSTEMS AND METHODS FOR MEASURING BIOMARKERS

The present application claims the benefit and priority of U.S. 62/641,299, filed on Mar. 10, 2018.

The present disclosure relates to devices, systems and methods for measuring biomarkers, more specifically to devices, systems and methods for measuring biomarkers in a non-invasive manner.

BACKGROUND

One of the most promising and at the same time rapidly growing healthcare areas is the wearable devices that assist individuals keeping track of their everyday activities. Preventive medicine and real time monitoring services are gaining an increasing emphasis driven by the increasing need for chronic disease management, patient empowerment, wellness and aging population support.

To date, there is a plurality of applications and services supported by modern smartphones and mobile applications using embedded or external sensing devices for capturing e.g. physical activity, fitness and sleep patterns, etc.

However, most of known devices are highly inaccurate, not standardized, and not considered as medical grade devices, but rather as fitness trackers. That is, there is no known wearable device achieving highly accurate readings of vital signs such as blood oxygen levels.

In addition, known devices may comprise limited functionalities and/or may be aesthetically not appealing to users for continuous or everyday use.

In conclusion, there is a need for providing wearable devices, systems and/or methods that provide a medical grade accuracy of a complete set of vital signs via non-invasive measurements without compromising comfort or aesthetic appeal.

SUMMARY

In a first aspect, wrist-watch back case for replacing a removable back case of a timekeeping device or to be attached thereto, is provided. The wrist-watch back case comprises a casing comprising a bottom wall and a side thereby defining an inner empty space and having at least five openings at the bottom wall. The back case also comprises an optoelectronic circuit board to be fitted in the inner space of the casing. The optoelectronic circuit board comprises at least two paired radiation sources to impinge radiation on user skin when the wrist-watch is worn by the user. Each source has a different emission wave length and at least one radiation detector to detect the reflected radiation exiting from skin and to transform it into a processable signal. The radiation sources and radiation detector are arranged in correspondence to the at least five openings.

A claimed casing enables transforming a timekeeping wristband device into a smart medical apparatus, capable of accurately measuring a plurality of health-related biomarkers without altering the functionality and/or the characteristics of the timekeeping device. The need of an extra display may also be avoided.

In addition, the back case enables a user to choose between replacing the replaceable back case or attaching the proposed back case to an existing back case thereby the apparatus is easy to use.

The claimed back case is simple and cost effective as the user does not need to buy a completely new device as the proposed back case permits using the user's own timekeeping device. As a result, the aesthetic design is neither altered nor compromised as the back case can also be attached to a timekeeping device (watch).

In addition, the use of a claimed back case ensures an optimal sensor-body contact with the radiation sources.

In some examples, the back case may further comprise radiation guiding elements.

In some examples, the back case may further comprise a temperature sensor for measuring user body temperature.

In some examples, the back case may further comprise fastening elements to attach the back case to a timekeeping device.

In some examples, the back case may further comprise a first thermally insulating layer to thermally insulate back casing.

In some examples, the radiation detector is a photodiode.

In some examples, the radiation detector may further comprise filters, e.g. optical filters. A photoplethysmogram (PPG) signal may be generated. A photoplethysmogram (PPG) is an optically obtained absorption signal. It may be acquired by using a radiation source which illuminates the skin and a radiation detector to measure changes in light absorption reflecting the volumetric variations of blood circulation.

In another aspect, a method for non-invasive measurements of biomarkers is provided. The method comprises providing at least two paired radiation sources having different wave lengths, illuminating the skin with the at least two radiation sources and capturing the radiation exiting from the skin. The method further comprises generating an absorption (PPG) signal, extracting the epochs from the PPG signal; identifying the pulses on the PPG signal and filtering the PPG signal. The filtering step is repeated for all pulses until each pulse is within a predetermined reliability range.

By using such a method an increased accuracy of biomarkers is provided and so medical grade measurements may therefore be obtained.

In some examples, the method may further comprise illuminating the skin with a predefined wavelength until the maximum gain is reached.

In some examples, the method may further comprise calculating an acceptable (artefact-free) derived PPG signal (PPGd).

In some examples, filtering the PPG signal comprises rejecting non-ideal pulses.

In some examples, the method may further comprise extracting features from the PPGd signal. A PPGd signal having a plurality of epochs comprising pulses may be provided and the pulses of each epoch of the PPGd signal may be separated.

In some examples, the method may further comprise outputting a feature set for calculating biomarkers.

In another aspect, a method for calculating blood oxygen level ($SpO_2$) is provided. The method comprises providing a PPGd signal, separating the PPGd signal into pulse waves and calculating the absorption/emission peaks. The method also comprises calculating RatioR from the absorption/emission peaks, calculating extinction coefficients of oxyhemoglobin and deoxyhemoglobin, and calculating unique wave propagation calibration coefficient (a).

In another aspect a method for calculating blood pressure (BP) is provided. The method comprises ensuring an ideal noise free environment, contacting the skin with a device according to aspects disclosed herein and estimating BP. Then BP is compared with a predetermined range, and the user is suggested to measure BP with conventional sphygmomanometer when the BP is out of the predetermined range.

In another aspect a system for non-invasive measurements of biomarkers is provided. The system comprises an illumination module comprising at least two paired radiation sources, a capture module comprising at least one radiation detector and a calculation module for calculating an absorption signal. The system also comprises a feature extraction module for extracting features from the absorption signal and a communication module for managing the communications between the calculation and feature extraction modules.

In another aspect a watchband to be attached around a wrist of a user in an adjustable manner for non-invasive measurements of biomarkers is provided. The watchband comprises a textile layer having perforations to adapt the degree of fixation, coupling elements for coupling the watchband to a watch face and a buckle coupled to an end of the wristband. The buckle has a frame and a pivoting prong coupled to the frame. The watchband also comprises a tightening mechanism for obtaining a predefined fixation on the wrist. The tightening mechanism comprises a ratchet gear having locking teeth in a predetermined angular range and a pivoting strut to engage the ratchet gear. The tightening mechanism may be arranged at a side of the buckle of a wristband or one tightening mechanism may be arranged at each side for better stability.

A tighten fixation and thus, an optimized sensor-body contact is thereby facilitated which improves and assures the accuracy of the measurements i.e. of the calculated biomarkers.

In another aspect a timekeeping device is provided. The timekeeping device comprises a wristband according to aspects disclosed hereinbefore, and a back case according to aspects disclosed hereinbefore.

In another aspect system for non-invasive measurements of biomarkers is provided. The system comprises a back case according to aspects disclosed hereinbefore, an interface module, and a mobile device for controlling signal acquisition procedure, acquisition mode and acquisition parameters as well as processing all the signals and performing the calculation methods as disclosed herein.

BRIEF DESCRIPTION OF THE DRAWINGS

Non-limiting examples of the present disclosure will be described in the following, with reference to the appended drawings, in which.

DETAILED DESCRIPTION

Figure 1:
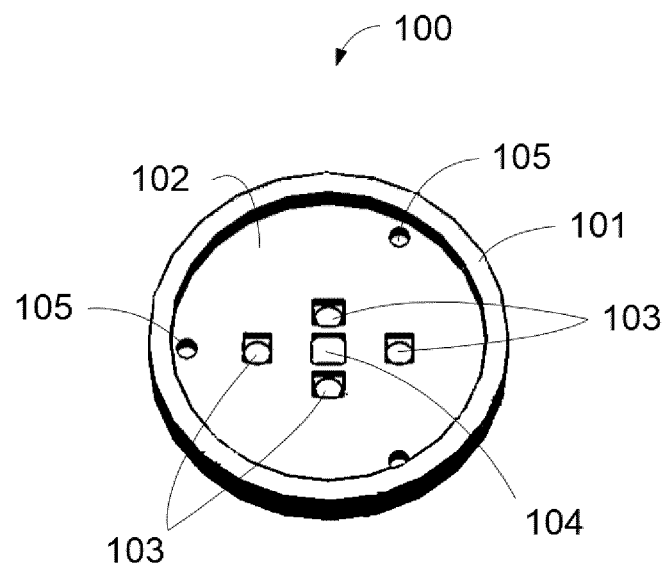
FIG. 1 schematically illustrates a back case according to an example.

FIG. 1 shows a back case 100 to be attached to an existing back case of a timekeeping device. The back case 100 may comprise a bottom wall 102 and a side wall 101 surrounding the bottom wall thereby forming an inner empty space for fitting an electronics circuit board (later on disclosed).

The back case 100 may be made of e.g. plastic, metal, carbon fiber or any other suitable material.

The bottom wall 102 may comprise openings 103, 104 for receiving an element of a circuit board and openings 105 for attaching the circuit board to the bottom wall 102.

The bottom wall may comprise a central opening, a pair of openings surrounding the central opening and openings near the periphery of the bottom wall.

In an example, the bottom wall 102 may comprise openings 103 for receiving radiation sources, an opening 104 for receiving a radiation detector and other elements e.g. a temperature sensor and openings 105 for fastening the electronics circuit board to the bottom wall. The diameter of each opening 103-105 may vary depending on the element to be received therein. For instance, openings 103 for receiving radiation sources may comprise a diameter smaller than the diameter of opening 104 for receiving a radiation detector.

In an example, the back case 100 may comprise an opening 104 for receiving a radiation detector arranged in the bottom wall 102 and four radiation source openings 103 arranged around and in the proximity of the opening 105 for receiving the detector. The four radiation source openings 103 may be arranged at 90 degrees with respect to each other and. A pair of such opposite, i.e. arranged at 180 degrees with respect to each other, radiator source openings 103 may be situated at a closer distance to the opening 104 than the other opposing radiator opening sources.

The bottom wall 102 may comprise any shape e.g. substantially rounded, elliptical, etc., for adapting to the watch face of a certain timekeeping device and therefore avoid part of the back case 100 from protruding out of the timekeeping face which may be uncomfortable and may even cause injuries to the user. In an example, the bottom wall 102 may be substantially circular and its diameter, i.e. the diameter of the back case 100, may be of about 30-50 mm. In an example, the diameter may be 38 mm. In another example, the diameter may be about 42 mm.

The back case 100 may, after inserting a circuit board therein, be attached to an existing back case of a timekeeping device by an adhesive provided on the surface of the side wall or by any other suitable method.

In some examples, the back case 100 may replace the existing back case of a timekeeping device.

Figure 2:
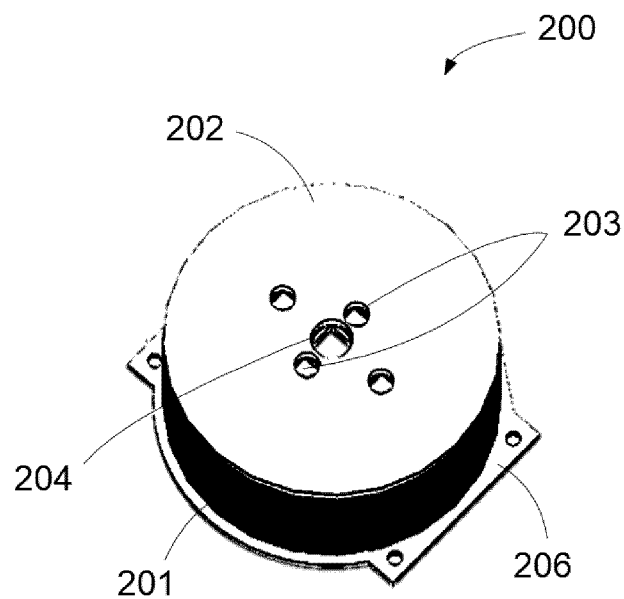
FIG. 2 schematically illustrates a back case according to an example.

FIG. 2 depicts an example of a back case 200 which differs from the back case 100 of FIG. 1 in that the side wall 201 may comprise fastening elements, e.g. laterally protruding flaps 206 to fasten the back case to the timekeeping device. In an example, the fastening elements may comprise screws (not shown) to provide a secure fastening of the back case to the timekeeping device.

In addition, the height of the side wall 201 may be different than that in the example of FIG. 1, thereby forming a deeper or shallower inner space.

The back case 100, 200 according to any of the disclosed examples may further comprise a first insulating layer (not shown) to insulate the inner space. In an example, the first insulating layer may be thermally insulating layer and/or a moisture insulating layer. The first insulating layer may be arranged at the sidewall, i.e. at the periphery of the back casing, thereby thermally and/or hermetically sealing the inner space there between when coupling the back case to a timekeeping device. A thermally conductive ring may be in contact with the skin and conduct the heat to the sensor, which is inside the casing. In an example, the conductive ring may be made of metal.

Figure 3:
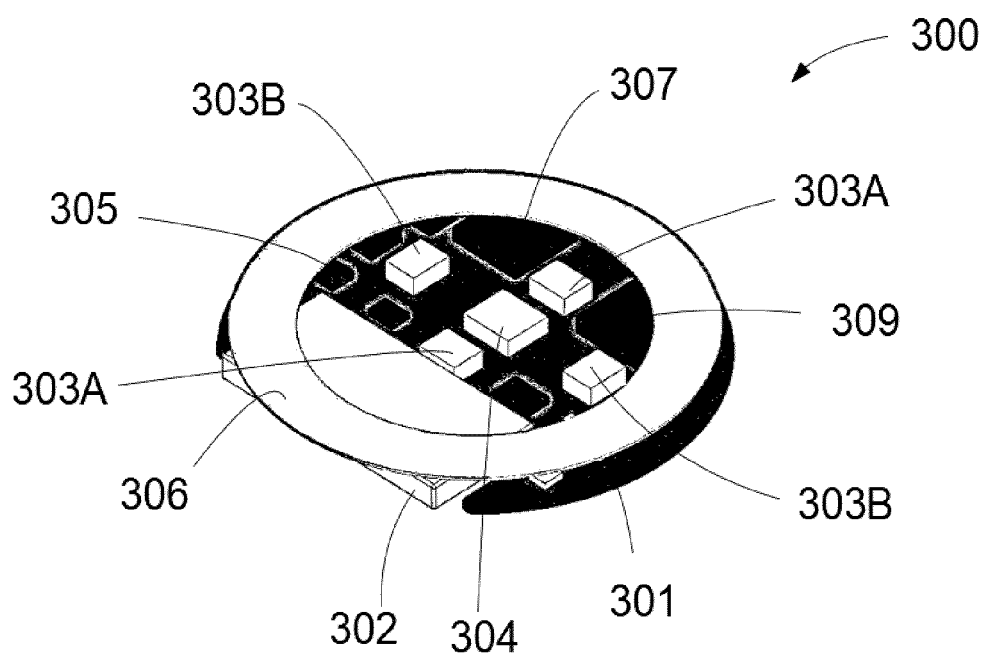
FIG. 3 schematically illustrates an optoelectronic circuit board according to an example.

FIG. 3 depicts a circuit board 300, e.g. an optoelectronic circuit board, to be fitted within a back case 100, 200 according to any of the disclosed examples. The optoelectronic circuit board 300 may comprise a base plate 301 e.g. a printed circuit board (PCB), in which different electronic and/or optoelectronic elements may be arranged. The optoelectronic circuit board 300 may have a shape corresponding to the shape of the bottom wall 102, 202 of a back case 100, 200 to be easily fitted therein.

The optoelectronic circuit board 300 may comprise at least two paired radiation sources 303A, 303B for generating emissions having two different wavelengths e.g. visible, near infrared (NIR), infrared (IR) or any combination thereof, thereby obtaining a different penetration degree into the skin.

The first paired radiation sources 303A may emit radiation of a first wavelength λ1 that may achieve a deeper skin penetration, i.e. may reach large arteries. Such first wavelength λ1 may be less sensitive to oxyhemoglobin content thereby yielding a more stable signal over the time and less dependent on temperature. The second paired radiation sources 303B may emit radiation of a second wavelength λ2. Such radiation may penetrate less in the tissues but may capture large intensity variations, i.e. may comprise greater absorptivity.

The at least two paired radiation sources 303A, 303B may emit radiation subsequently, i.e. the emission may not be simultaneous.

The paired radiation sources 303A, 303B may impinge the body in a pulsed, continuous, frequency modulated, amplitude modulated, polarization or phase modulated mode in order to detect the intrinsic components of the tissue. In an example, the radiation sources 303A, 303B may be LED emitters or laser diodes.

The optoelectronic circuit board 300 may also comprise at least a radiation detector 304 e.g. a photodiode, to detect the light exiting from the body. The radiation source may also be provided with filters, i.e., dielectric coatings, diffractive elements or any type of wavelength selection element (not shown) and may generate a photoplethysmogram (PPG) signal.

The optoelectronic circuit board 300 may comprise a first set of radiation guiding elements (not shown) to be arranged between the radiation detector 304 and patient skin for providing a coupling of the radiation exiting from the user skin and thereby improve the accuracy and reliability of measurements. The optoelectronic circuit board 300 may comprise a second set of radiation guiding elements (not shown) to be arranged between each of the paired radiation sources 303A and 303B and user skin for providing an optimum coupling of the radiation entering the user skin and thereby improve the accuracy and reliability of measurements. The guiding elements may be microlenses, Fresnel lenses, diffraction elements, optical fibers, waveguides, photonic structures, etc.

The optoelectronic circuit board 300 may also comprise a power module comprising rechargeable battery 302 e.g. a lithium-ion polymer battery, and a battery charging element 306 which may charge the battery through wireless electromagnetic induction. The battery charging element 306 e.g. a charging coil, may be arranged on the periphery, i.e. around, the optoelectronic circuit board 300. Such power module may further comprise at least two voltage regulators to stabilize voltages of all electronic and optoelectronic components.

The optoelectronic circuit board 300 may comprise an analog to digital front end (AFE) 307, e.g. a system on chip (SoC). The AFE 307 may comprise an analog to digital converter (ADC) which may transform the detected exiting radiation analogic signal of the radiator detector into a digital signal e.g. of 22 bits. The AFE 307 may further control timings, sampling and radiation intensity parameters of the data acquisition, i.e. of the radiation entering and exiting the user body.

In some examples, the AFE 307 may not drive more than two different paired radiation sources (emitters) simultaneously, therefore the AFE 307 may comprise a selection circuit (not shown) for selecting paired radiation sources to impinge radiation on user skin. The selected paired radiation sources may emit radiation having Visible wavelength only, Near Infrared (NIR) wavelength only, Infrared (IR) wavelength only, Visible and NIR wavelength interchanged, NIR and IR wavelength interchanged, and Visible and IR wavelength interchanged.

In an example, there may be as many selection circuits as radiation source pairs.

In addition, the optoelectronic circuit board 300 may comprise a temperature and inertial measurement unit (TIMU) 305, e.g. a low power integrated microelectromechanical system (MEMS).

The TIMU 305 may comprise a temperature sensor and also an inertial measurement unit, e.g. an inertial sensor, which may comprise a plurality of magnetic field channels and a plurality of acceleration channels, each having adjustable scales. The measured signals of both magnetic field and acceleration channels may be used e.g. as artefact rejection, PPG signal quality assessment, etc.

In an example, the adjustable scales may be ±2, ±4, ±8 and ±12 gauss magnetic full scale, and ±2, ±4, ±6, ±8 or ±16 linear acceleration full scale.

In an example, the TIMU may comprise 3 magnetic field channels and 3 acceleration channels.

The inertial sensor of the TIMU 305 may measure the acceleration of the optoelectronic board and thus of the back case.

The temperature sensor may comprise a second thermally insulating layer (not shown) arranged for thermally decoupling the temperature sensor from remaining electronic components of the optoelectronic circuit board 300. By thermally decoupling the temperature sensor and together with the first thermally insulating layer, arranged between the back case and a timekeeping device the temperature measurement accuracy is improved. A thermally conductive ring is in contact with the skin and conducts the heat to the sensor, which is inside the casing.

The optoelectronic circuit board 300 may further comprise a control and communication module (MCUBT) 309, e.g. a system on chip (SoC), which may communicate with the AFE and the TIMU to enable a fast data acquisition i.e.

at sampling rates of at least 500 Hz for the AFE and at least 100 Hz for the TIMU. The control and communication module 309 may further communicate with an external (mobile) device, e.g. a smartphone, a tablet, a computer, etc., to provide the acquired data. Such an external device may control the signal processing and the measuring process. In some example, an external device may also control the selection circuit of the AFE.

The control and communication module 309 may comprise a microprocessor and a communication module, e.g. Bluetooth.

In an example, the optoelectronic circuit board 300 may further comprise optoacoustic emitters and receivers (not shown). The acoustic emitters and radiation sources may be multiplexed.

In an example, the optoelectronic circuit board 300 may further comprise an interface module (not shown). The optoelectronic board may comprise a control module for initiating and controlling the data acquisition parameters, a communication module for managing the communications with an external mobile device and two voltage regulators. The optoelectronic board may additionally comprise an analogue to digital front end for managing the conversion of the analogue signal received by the radiation detector to a digital one, and for controlling the radiation sources.

In an example, the optoelectronic circuit board 300 may be fixed to the bottom wall 102, 202 of the back case 100, 200 by adhesive, by coupling elements or any other suitable method.

Once the optoelectronic circuit board 300 is assembled within the inner space of the housing of a back case 100, 200 according to any of the disclosed examples, the resulting back case may be ready to be attached to or to replace an existing back case of a wrist watch or other timekeeping device. When the proposed back case is to be attached to an existing back case a thin cover may be placed between the case and the watch body for protection, e.g. against moisture accumulation.

The assembled back case, i.e. the back case having the optoelectronic circuit board within the housing, may have a thickness determined by the thickness of the height of the side wall. In an example, the battery may have a thickness of about 1.9 mm, the charging coil may have a thickness of about 0.4 mm and the side wall a height of about 0.8-2 mm.

In an example, the optoelectronic circuit board 300 may comprise more than two paired radiation sources e.g. near infrared, short wave infrared, infrared, mid-infrared, etc. for measuring tissue constituents such as water, lipids e.g. yellow and brown fat, and glucose. Additional and related biomarkers, e.g. hydration, lipid metabolic activity, blood sugar levels and glucose metabolic activity, may also be then calculated.

The back case and the optoelectronic circuit board may be manufactured e.g. by CNC machining, milling, moulding, press fitting, 3D printing, etc. Any suitable material such as metal e.g. stainless steel, titanium, aluminium, gold, silver; plastic, composite materials, carbon fibre or any combination may be used to manufacture a back case and/or an optoelectronic circuit board according to any of the disclosed examples.

Figure 4:
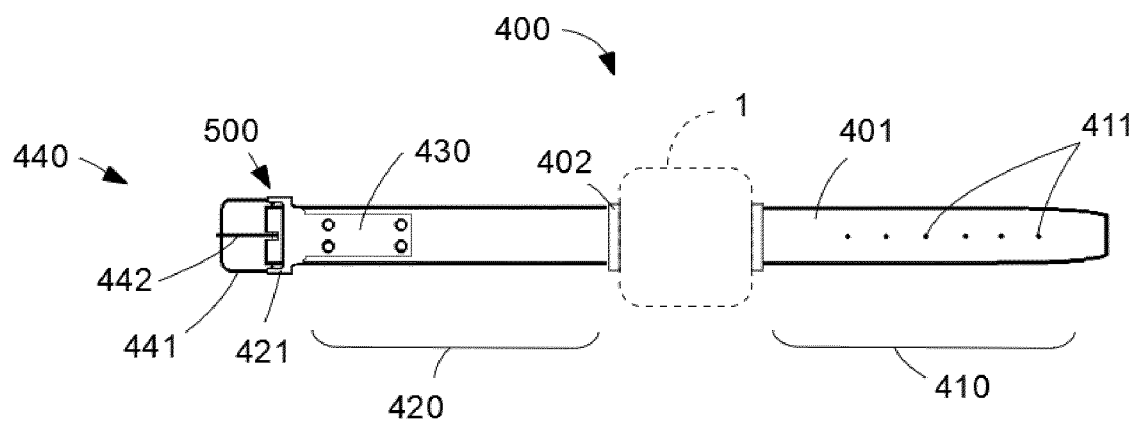
FIG. 4 schematically illustrates a watchband according to an example.

FIG. 4 depicts the bottom view of a watchband or a timekeeping band 400 to be attached around a user wrist in an adjustable manner. The watchband 400 may comprise a flexible layer 401 e.g. made of fabric, plastic, leather, metal, etc., that may have a first 410 and a second portions 420 to be coupled to the watch body 1 of a timekeeping device. The watchband 400 may further comprise coupling elements 402 for coupling the watch face 1 to the flexible layer 401.

The first portion 410 may comprise adjusting elements 411, e.g. perforations, in order to enable the user to adapt the watchband to the size of user wrist. The second portion 420 may comprise a buckle 440 arranged at an end 421 of the flexible layer. The buckle 440 may comprise a frame 441 and a pivoting prong 442 coupled to the frame. The pivoting prong 442 may be introduced in a specific adjusting element to adjust the watchband to the user wrist.

In order to ensure a proper counterforce when fastening the watchband 400 i.e. when pulling up the buckle, around the wrist of the user, the watchband may further comprise a solid plate 430 e.g. made of metal, which may be arranged below the flexible layer.

The watchband 400 may replace the existing fastening system of a timekeeping device thereby ensuring a tighten fixation which aids to maintain the sensor-body contact pressure and improves the signal while avoiding vasoconstriction and/or user discomfort.

Additionally, the watchband 400 may further comprise a tightening mechanism 500 that may be arranged in the frame of the buckle 440. The use of the tightening mechanism 500 enables obtaining a predefined fixation on the wrist and thereby improving the sensor-skin contact and the accuracy of measurements.

Figure 5:
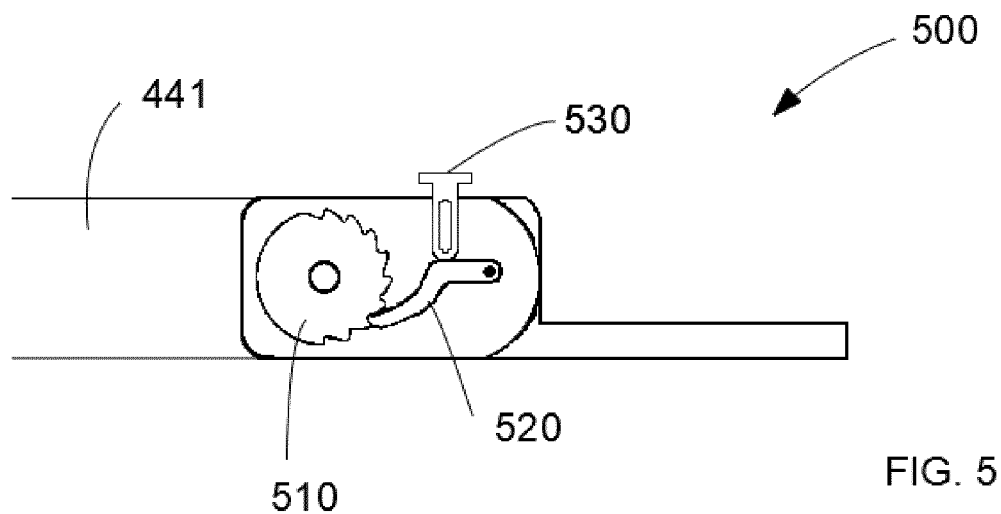
FIG. 5 schematically illustrates a tightening mechanism according to an example.

FIG. 5 shows a tightening mechanism 500 that may be arranged at a side of the buckle. The tightening mechanism 500 may comprise a ratchet gear 510 having a plurality of locking teeth arranged at the periphery, over a predetermined angular range and facing a pivoting strut 520 that may engage the teeth. The mechanism 500 may further comprise an unlocking mechanism 530, e.g. a knob, and compression spring (not shown) for holding the unlocking mechanism 530 against the pivoting strut against the ratchet gear 510.

In order to unlock the mechanism, the user may press the unlocking mechanism and release the pivoting strut.

The buckle can freely move in the opposite direction to locking thereby allowing the watch band to form a circular shape around the wrist when no measurement is taken.

In an example, the watchband 400 may comprise two tightening mechanisms 500 arranged at opposite sides of the buckle.

Figure 6:
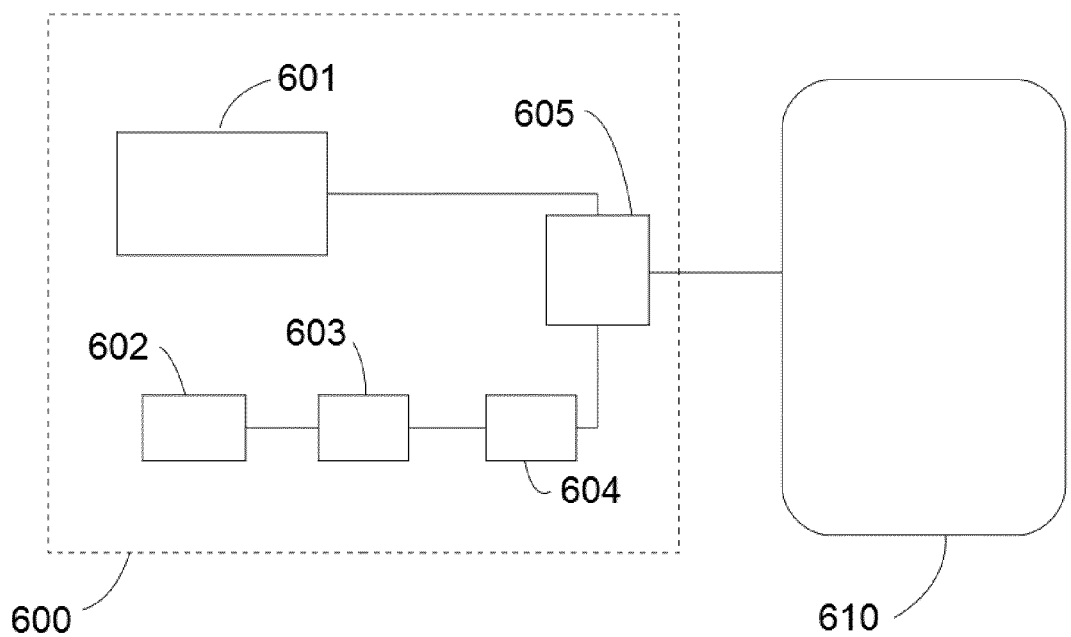
FIG. 6 schematically illustrates a system according to an example.

FIG. 6 depicts a system 600 which may comprise an illumination module 601 comprising at least two paired radiation sources according to any of the disclosed examples for illuminating user skin, a capture module 602 comprising at least one radiation detector for detecting the light exiting from the user according to any of the disclosed examples and a calculation module 603 for calculating an absorption signal. The system 600 may further comprise a feature extraction module 604 for extracting features from the absorption signal and a communication module 605 for managing the communications between the calculation and feature extraction modules. In an example, the communication module may further manage communications between the system 600 and an external communication device 610.

Figure 7:
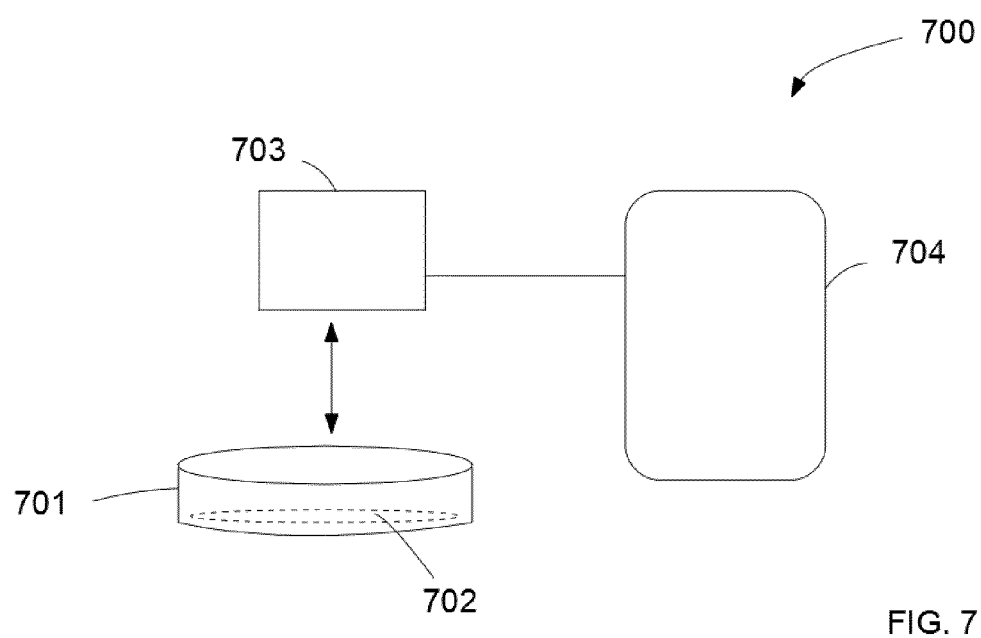
FIG. 7 schematically illustrates a system according to an example.

FIG. 7 depicts a system 700 for non-invasive measurements of biomarkers which may comprise a back case 701 according to any of the disclosed examples and wherein the back case may comprise an optoelectronic circuit board 702 according to any of the disclosed examples. The system 700 may comprise an interface module 703 and a mobile device 704 for controlling signal acquisition procedure, acquisition mode and acquisition parameters. In an example, the system 700 may further comprise a detachable device for obtaining measurements in a different body position. The detachable device may be adhered to user body e.g. in a removable manner. In an example, the detachable device may be a sticker.

Figure 8A:
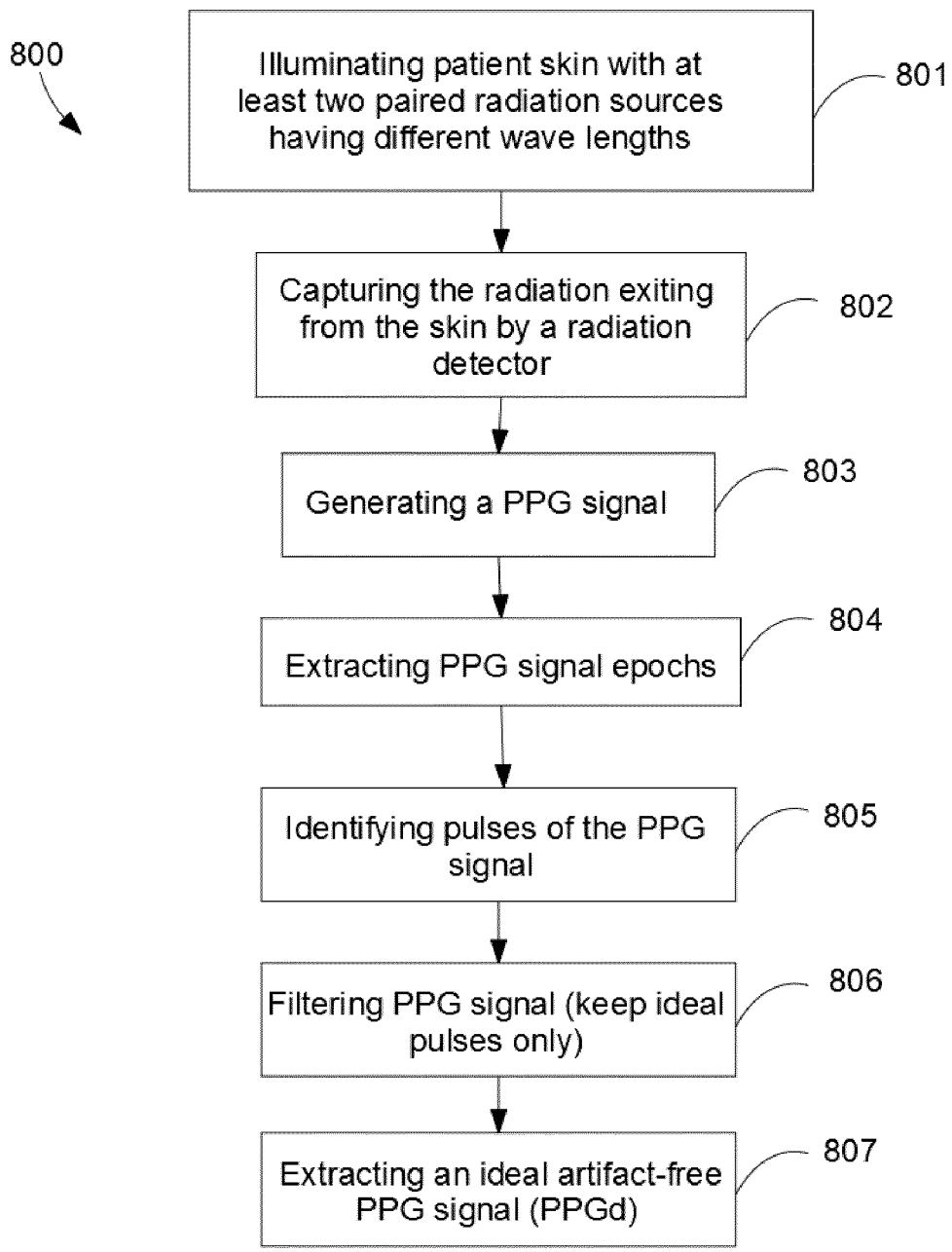
FIG. 8A schematically illustrates a flow chart of a method according to an example.

FIG. 8A depicts a block diagram of a method 800 for non-invasive measurements of biomarkers which may be implemented with a back case comprising an optoelectronic circuit according to any of the disclosed examples. Firstly, the at least two paired radiation sources having different wave lengths λ1, λ2 may be provided.

In an example, the first wave length λ1 may achieve deeper penetration than the second wave length λ2 which may only achieve superficial penetration. The first wave length λ1 may be, e.g. red light, infrared (IR) or near infrared (NIR), and when comparing with second wave length λ2, it may be less sensitive to oxyhemoglobin and therefore more stable over time, and less sensitive to temperature. The second wave length λ2, e.g. green light, may capture large intensity variations as it may have greater absorption of oxyhemoglobin and deoxyhemoglobin and so the cardiac cycle may be better reflected. By using such different wave lengths a better signal to noise ratio (SNR) may therefore be achieved. In addition, the second wave length λ2 may be more sensitive to temperature and vasodilatation/constriction.

Once a back case is attached or coupled to a timekeeping device and the latter fastened e.g. around user wrist, the user skin may be illuminated, in block 801, with at least two paired radiation sources having different wave lengths. The acquired signal and the skin penetration may therefore be improved. In an example, the skin may be interchangeably illuminated by the two paired radiation sources. In an example, the skin may be firstly illuminated by an IR or NIR radiation wave length to get robust PPG signal in reflectance mode.

Then, in block 802, the radiation exiting from the skin, i.e. the reflected radiation, may be captured, e.g. by a radiation detector arranged on the optoelectronic circuit board of the back case, and an absorption signal, e.g. a PPG signal, may be generated, in block 803, by the radiation detector. Then, in block 804, the signal epochs or epochs of the PPG signal may be extracted. Signal epochs are signal segments or signal frame lengths of a predefined length which may be long enough to facilitate robust statistical information and short enough to capture non-stationary information. In an example, the length of each epoch may be of about 8 seconds to accommodate 8-10 heart cycles within.

Pulses and/or pulse morphology of the PPG signal may then, in block 805, be identified and the PPG signal may then be filtered, in block 806, to get ideal artefact free PPG signal. In an example, the filtering may comprise rejecting whole pulses.

The filtering may then be repeated for all pulses of every signal epoch until each signal epoch is within a predetermined reliability range.

Then, in block 807, filtered pulsed, i.e. non-removed pulses, may be collated thereby forming an acceptable (artefact free or ideal) derived PPG signal. The derived PPG signal (PPGd) may then be used for calculating the biomarkers (later on disclosed).

In an example, the method 800 may further comprise assessing $SNR_{PPG}$ of the PPG signal to verify whether $SNR_{PPG}$ is within an acceptable range of values. The $SNR_{PPG}$ of the PPG signal may indicate the level of the clinically useful signal to the level of background noise. In an example, the $SNR_{PPG}$ may be the ratio of filtered PPG signal variance to the unfiltered raw signal, i.e. noise, variance.

In an example, the method may further comprise assessing the PPG signal quality which may be performed e.g. by Kurtosis, Skewness or any other suitable method. The Skewness ($S_{PPG}$) is defined as:

$$S_{PPG} = \frac{E(x - \mu_x)}{\sigma_x^3}$$

where x is the raw, i.e. unfiltered, PPG signal, $\mu_x$ and $\sigma_x$ are the empirical estimates of the mean and standard deviation of x, and E is the expected value operator.

In an alternative example, Perfusion index ($PI_{PPG}$) of the PPG signal may be used to calculate PPG signal quality. The $PI_{PPG}$ is the ratio of the pulsatile blood flow (AC) to the non-pulsatile or static blood in peripheral tissue (DC), and represents the represents the difference of the amount of light absorbed through the pulse of when light is transmitted through the tissue. The $PI_{PPG}$ may be calculated as:

$$PI_{PPG} = \frac{AC}{DC} \times 100 = \frac{(\text{emmission peak} - \text{absortion peak})}{\mu_x} \times 100$$

Wherein $\mu_x$ is the raw unfiltered signal mean, and emission and absorption peaks are calculated on the filtered signal.

In case the SNR is out of the predefined range of values, the skin may be further illuminated with a predefined wave length radiation e.g. 916-960 nm, IR/NIR wavelength, until the maximum possible gain limits of the illumination driver is reached. The $SNR_{PPG}$, $PI_{PPG}$ or $S_{PPG}$ may then be re-evaluated and, in the event that a non-working signal persists and no further gain increase may be achieved, the skin may be illuminated by alternative radiation having a wave length of e.g. 510-522 nm, corresponding to green colour wavelength. The amplification gain can be also increased in order to ensure better SNR.

In an example, temperature may also be closely monitored, since cold temperature conditions may significantly reduce PPG signal quality, whereas warm temperature conditions may improve the quality of the PPG signal e.g. up to four times. Warm temperature conditions ensure reliable measurements related to peripheral extraction and circulation.

Figure 8B:
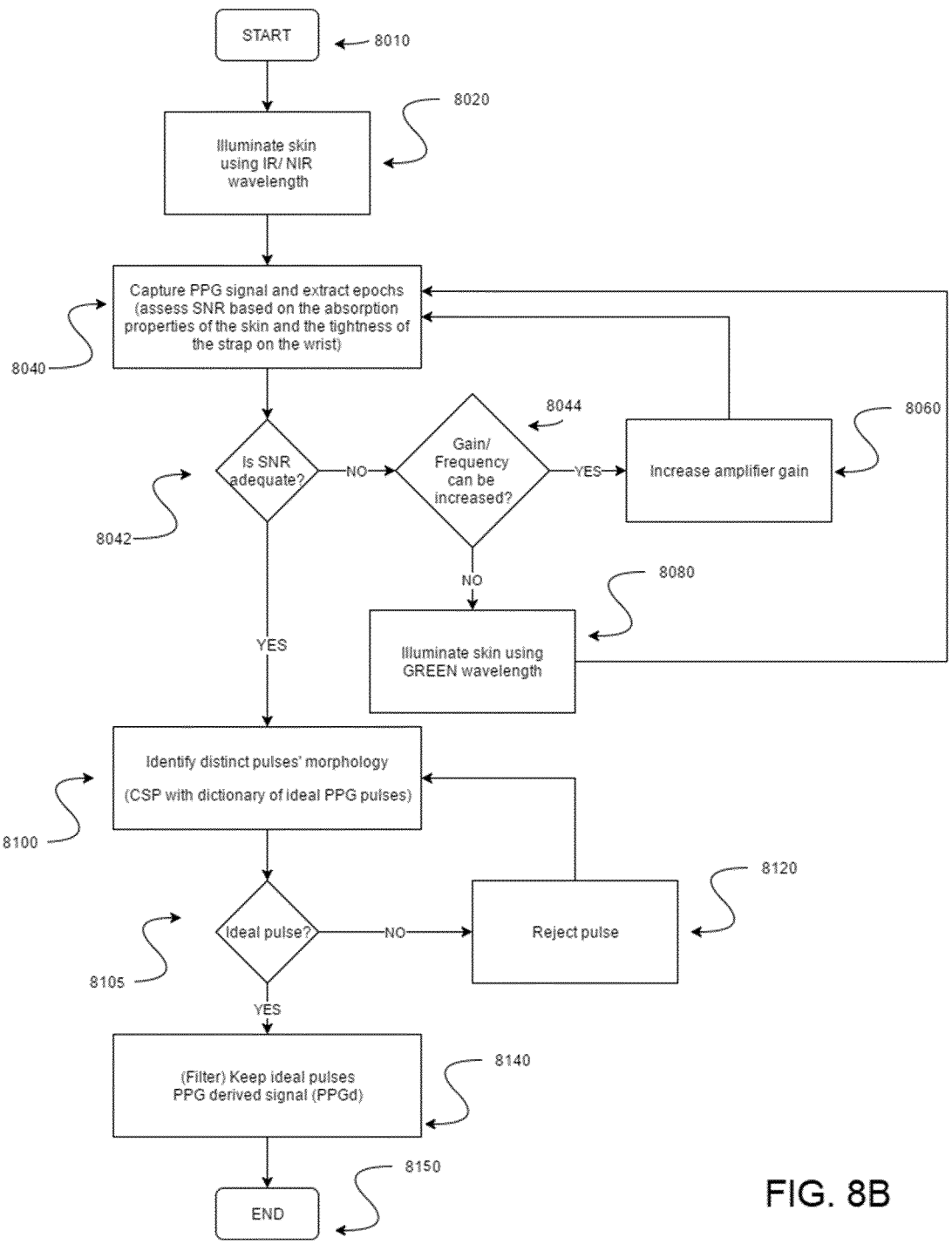
FIG. 8B schematically illustrates a flow chart of a method according to an example.

FIG. 8B schematically illustrates a detailed implementation of the method of FIG. 8A. In block 8010 the method may be initiated when a condition is met (e.g. user selection, a predetermined time interval is reached, a time of the day etc.). In block 8020 the skin may be illuminated using e.g. IR/NIR wavelengths. In block 8040 a PPG signal may be captured and epochs may be extracted. The SNR may be assessed based on the absorption properties of the skin and the tightness of the strap around the wrist of the user. In decision box 8042, it may be determined if the SNR assessed is acceptable. If the SNR is determined to be not acceptable then in decision box 8044 it may be determined if the gain or frequency of the signal may be increased. If the gain can be increased, then in block 8060 the amplifier gain is increased and the method moves back to block 8040. If in decision box 8044 it is determined that the gain or frequency cannot be further increased, then the skin may be illuminated using a green wavelength in box 8080 and the process moves back to box 8040. Now, if after the aforementioned feedback control loop involving optimizing timing, intensity, gain or switching wavelength, the SNR is determined to be acceptable in decision box 8042. Then in box 8100 the distinct pulses' morphology may be identified to meet a predefined PPG signal template considered as ideal. By using a plurality of template matching algorithms, such as the Common Spatial Patterns (CSP) technique, template subtraction, Principal/Independent Component Analysis (PCA/ICA), simple Correlation or alternative, that may compare the actual signal with the template signal a similarity may be identified. A dynamic time warping may be used to stretch each beat to match the ideal running template. This process may be repeated for every pulse in each signal epoch until an ideal PPG derived signal (PPGd) is captured in box 8140. The process may then end in box 8150. As mentioned, the epoch is defined as the signal frame length able to accommodate about 8 to 10 heart cycles, long enough to capture robust statistical signal information, yet short enough to capture nonstationary information. Decision box 8105 may determine if pulse is acceptable and in box 8120 suboptimal pulses may be rejected.

Figure 9:
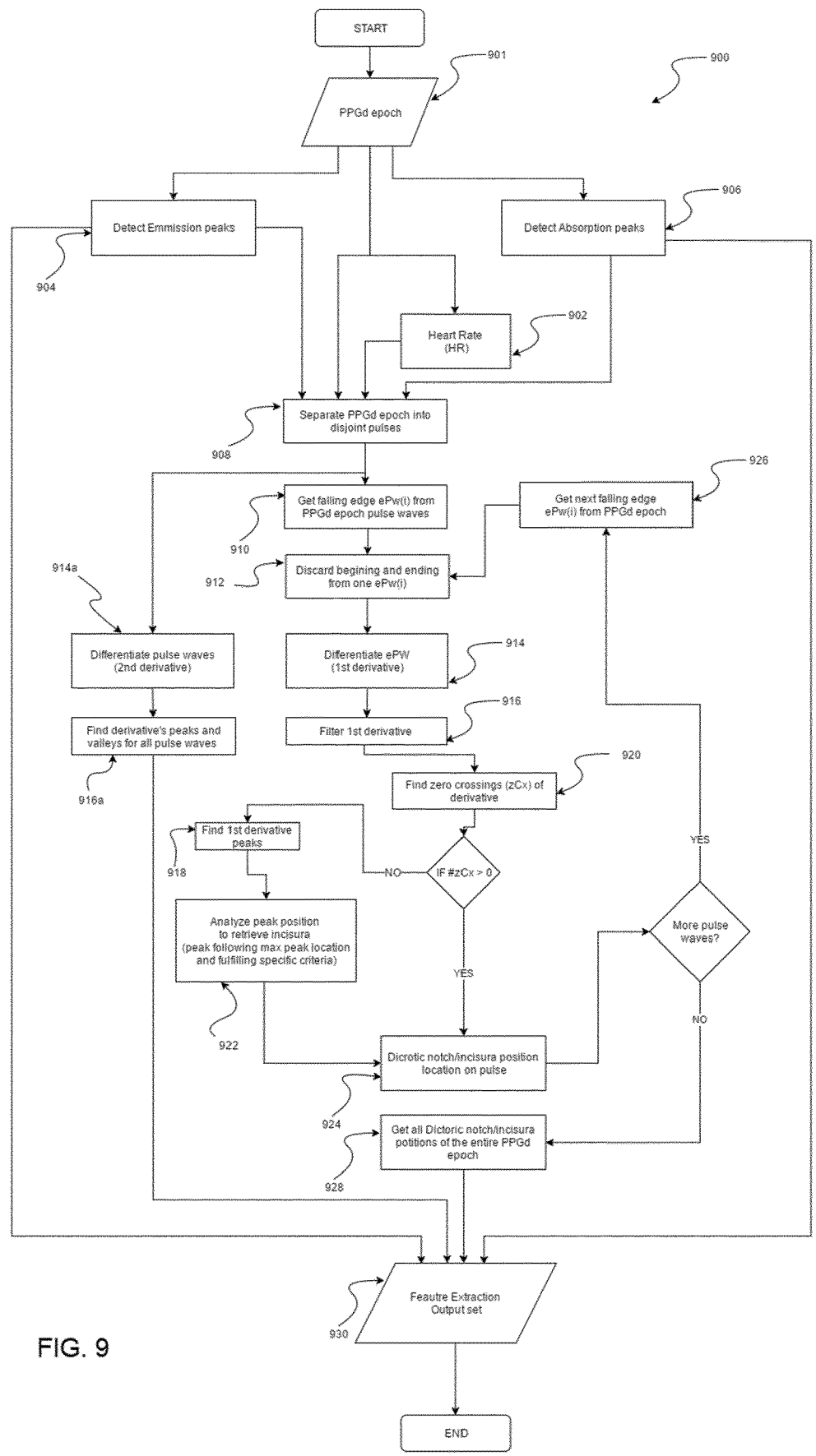
FIG. 9 schematically illustrates a flow chart of a method for extracting features according to an example.

FIG. 9 depicts a block diagram of a method 900 for extracting a feature output set which may be used to calculate biomarkers. Biomarkers may include Heart Rate (HR), Heart Rate Variability (HRV), Blood Oxygen Level ($SpO_2$), Cardiac Output (CO), Blood Pressure (BP), Respiratory Rate (RR), Arterial Stiffness (AS), Blood Flow Volume (BFV), Temperature and Activity tracking, etc.

Firstly, a PPGd signal e.g. the signal calculated from method 800, comprising a plurality of epochs having pulses may be provided, in block 901. The pulses of the PPGd signal may, in block 908, be separated.

In addition, the falling edge ePW(i) of each pulse (i denotes each pulse) may be extracted, in block 910, and the beginning and end tails of each ePW(i) may be discarded, in block 912, to eliminate edge discrepancies. To that end an empirically defined threshold value, e.g. equal to a length segment of 0.2*HR seconds, may be used.

The first derivative of each ePW(i) may then be calculated, in block 914, and filtered, in block 916, e.g. by low pass filter, in order to smooth out high frequency content. In an example, a moving average filtering with windows size of 31 samples may be used for filtering the first derivative.

The filtered first derivative may then be used to find the zero crossings (zCx), in block 920, e.g. using a step by step zero-crossing adaptive/non-adaptive technique.

In the event the zero crossings are found, their location may be determined and a respective ePW(i) dicrotic notch/incisura position may be found and assigned, in block 924, and such value stored in a memory device. The algorithm may be moved to the subsequent pulse, in block 926. The process may be repeated for all the pulses of the PPGd signal. We use the terms dicrotic notch and incisura to refer descriptively to the two possible positions of the notch. In the first case, (if the position is matched with an upstroke) we name it to be a "dicrotic notch", whether in the latter case, (if the position matches an inflection of the waveform) we will refer to it as an incisura.

On the contrary, in the event the zero crossings are not found, the peaks of first derivative of ePW(i) may be found, in block 918, and may be used to analyse each peak position in a descending order thereby to locating the peak corresponding to the incisura peak, in block 922. In an example, the selection of the peak may be based on position criteria with respect to the inter-beat time.

The output of block 922, may then be evaluated and used to determine the incisura position if it fulfils certain inclusion criteria, as follows: Disjoint pulses (908) are identified to be: upstrokes (upslope), or downstrokes (downslope) and inflections—based on the bending pattern of the pulse under study. The "dicrotic notch and/or incisura peak" is identified if one or more of the following criteria are met: a downstroke followed by a small upstroke and/or a downstroke followed by an inflection and an upstroke and/or a downstroke followed by an inflection and another downstroke. If more than one of these is identified, we select the one with the higher slope (negative/positive) curvature in the respected segment of question.

The algorithm may be moved to the subsequent pulse, in block 926.

In parallel to the separation of the pulses of the PPGd signal, the emission and absorption peaks of the PPGd signal may similarly be detected, in blocks 904 and 906, respectively, e.g. by using an algorithm based on geometric definition of signal trends and the statistical definition of peaks and valleys.

Additionally, the method 900 may further comprise calculating the second derivative of the PPGd signal, in block 914a, after separating the pulses of the PPGd signal. Then, the maximum and minimum peaks of the second derivative of the PPGd signal may be found, in block 916a, and the ratio of the maximum peak to the minimum peak may be calculated.

After processing all PPGd's pulses, all epoch's dicrotic notch/incisura may be retrieved, in block 928, and a feature output set may be calculated, in block 930, by adding the emission and absorption peaks latency and amplitude, the peak and valley latency of the PPGd's second derivative, as well as the computed epoch's HR (902) that may be calculated using e.g. dominant frequency extraction techniques or time domain detection techniques (i.e. autocorrelation).

The output feature set (f1-f8) may comprise: Pulse Transit Time (PTT), defined by the difference in latency within each pulse between the dicrotic notch and the absorption peak of the same pulse (f1), Amplitude/Latency of emission peak (f2), Amplitude/Latency of absorption peak (f3), Amplitude/Latency of dicrotic notch/incisura peak (f4), Heart Rate (HR) (f5), Time span between Maximum peak of first derivative and dicrotic notch/incisura peak of PPGd pulse (f6), the second derivative time span between maximum and minimum peak (f7) and PPGdIR ratio of PPGd epoch emission and absorption peak amplitude (f8).

In an example, the output features may then be used to compute the biomarkers for instance by method 1000 (later on disclosed).

Figure 10:
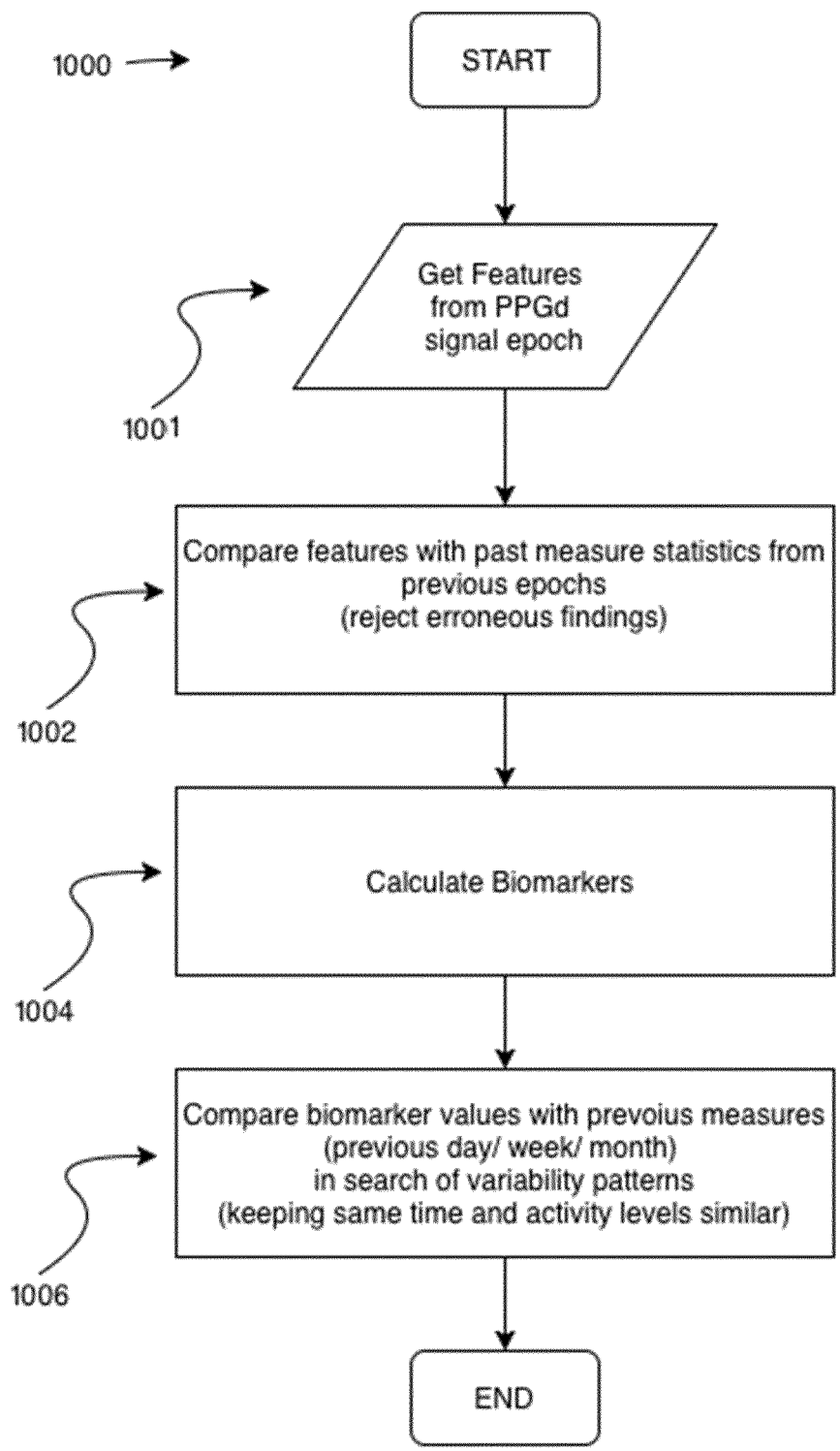
FIG. 10 schematically illustrates a flow chart of a method for calculating biomarkers according to an example.

FIG. 10 depicts a block diagram of method 1000 for calculating biomarkers, which may be subsequent to method 900 of FIG. 9. Firstly, the features may be extracted from the PPGd signal, in block 1001, and, in block 1002, the extracted features may be compared with previously stored features. In the event of statistically significant non-matching features, such features may be rejected.

The biomarkers may then be calculated, in block 1004, and calculated biomarkers may be compared, in block 1006, with values of previous measures e.g. of previous day, week, month, etc., in search or variability patterns i.e. capture at same time and similar activity level.

Figure 11:
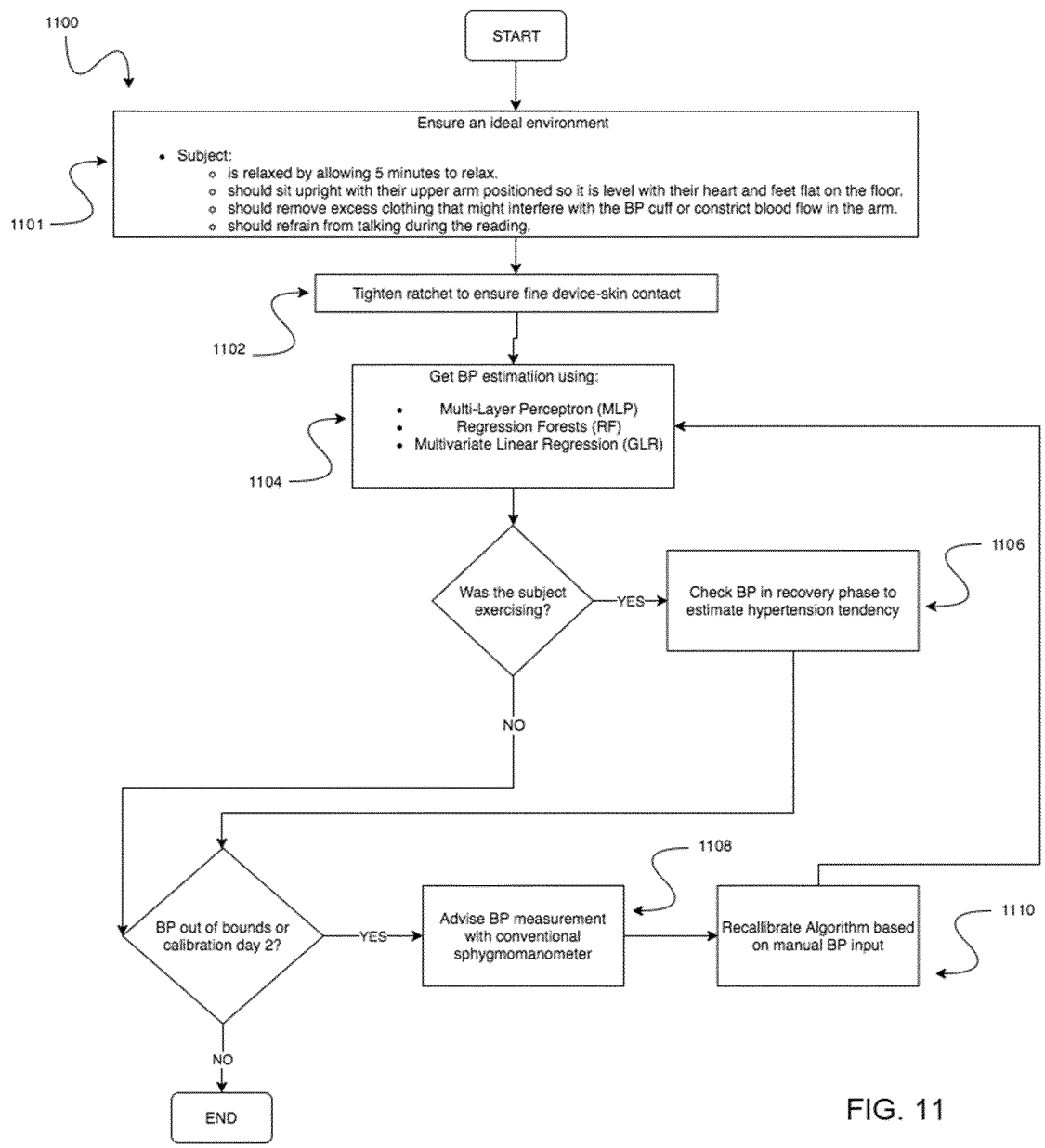
FIG. 11 schematically illustrates a flow chart of a method for calculating blood pressure according to an example.

FIG. 11 depicts a method 1100 for calculating Blood Pressure (BP) which may accurately estimate the BP using an output feature set f1-f8 calculated according to any of the disclosed examples. Firstly, an ideal noise free environment may be secured, in block 1101.

To get a noise free environment and improve the measurements, the user may be in a resting position, e.g. sitting upright on a chair. The user may use a system for non-invasive measurements according to any of the disclosed examples, i.e. comprising at least a back case, an interface module and a mobile device, attached thereto. In an example, the device may be leveled with the user heart and the feet flat on the floor.

In order to avoid obstructing blood flow, the excess of clothing or anything that could possibly block unobstructed blood flow in the arm may be removed. As a precautionary measure, reading or talking while taking measurements should be avoided for ensuring proper measurements. Before taking the first measurement, the user may tighten the watchband, in block 1102, e.g. via a tightening mechanism according to any of the disclosed examples, and thereby ensure a firm contact to the skin without risking overtightening. A first measurement may then be taken, after e.g. 5 minutes to allow for the individual to relax and the BP may then be estimated, in block 1104.

Blood Pressure (BP) is related to multiple factors such as blood hemodynamics, blood density and arterial physical properties i.e. thickness, diameter, and elasticity, stroke volume, heart rate, cardiac output, peripheral resistance, circulating blood volume, blood vessels, nervous system, circulatory system, respiration, emotion and other anthropic factors.

In an example, the method 1100 for calculating BP i.e. both systolic (SBP) and diastolic (DBP) blood pressures, relates to the features f1-f8 which may be closely selected to match different physiological properties of the cardiovascular system under study e.g. for reflecting peripheral resistance, vessel elasticity, cardiac output, blood volume and contribute to both the SBP and DBP calculation. Contrary to known PPT-based models, method 1100 is heavily depended on the dicrotic notch identification that carries significant physiological information. In method 1100 a particular attention may be paid on getting optimal signal quality from the wrist. All measurements and calculations may be performed by using a noise free, high quality PPGd signal.

The output features f1-f8 may be subjected to both linear and nonlinear multivariate analysis to build a BP estimation model.

In an example, Mean Square Error (MSE) loss function of either Multi-Layer Perceptron (MLP) or Regression Forests (RF), may be used to perform machine learning. Thereby an improved performance over time may be achieved, as compared to the faster Multivariate Linear Regression method (GLR).

In another example, ensemble learning may be used, that is, MLP, RF and GLR may be combined in order to improve the confidence of the BP estimation using majority voting. All BP models may be trained, i.e. calibrated, to output the widely used mmHg sphygmomanometer scale.

In another example, the user height, age, gender and health status may also be taken into account to derive BP measurements in each PPGd epoch.

For the training and validation phase, a static BP estimation experiment on 50 healthy normotensive adults (25 men and 25 women) with an age range 26-44 may be used. Assuming that the user was not exercising just before taking the measurement, the activity state may automatically be extracted from the TIMU sensor of the device, in block 604, BP estimation may be evaluated and in the event that BP moves outside of the bounds of normalcy, the user may be advised, in block 1108, to get an additional measurement with conventional sphygmomanometer.

In such a case, the values of three successive sphygmomanometer measurements, e.g. taken with an interval of 1 minute, may then entered e.g. manually, into a user interface, e.g. via a mobile app. In an example, the system may be retrained i.e. recalibrated, to take account for the manually entered measurements and the difference with respect to estimated BP values, in block 1110.

The estimation error is found to increase one day after model training, with no further significant increase, afterwards. A bit shifted (erroneous) blood pressure value may be provided the first day after initial calibration. Hence, the user may be prompted to recalibrate the system after one day in order to properly account for possible BP prediction power loss.

In the event the method is used while exercising, the system may be capable of evaluating BP in the recovery phase to estimate, in block 1106, the hypertension tendency of the user. In an example, the recovery phase, blood pressure may be hypertensive if a value of 140/90 mm Hg is exceeded in the fifth minute.

Figure 12:
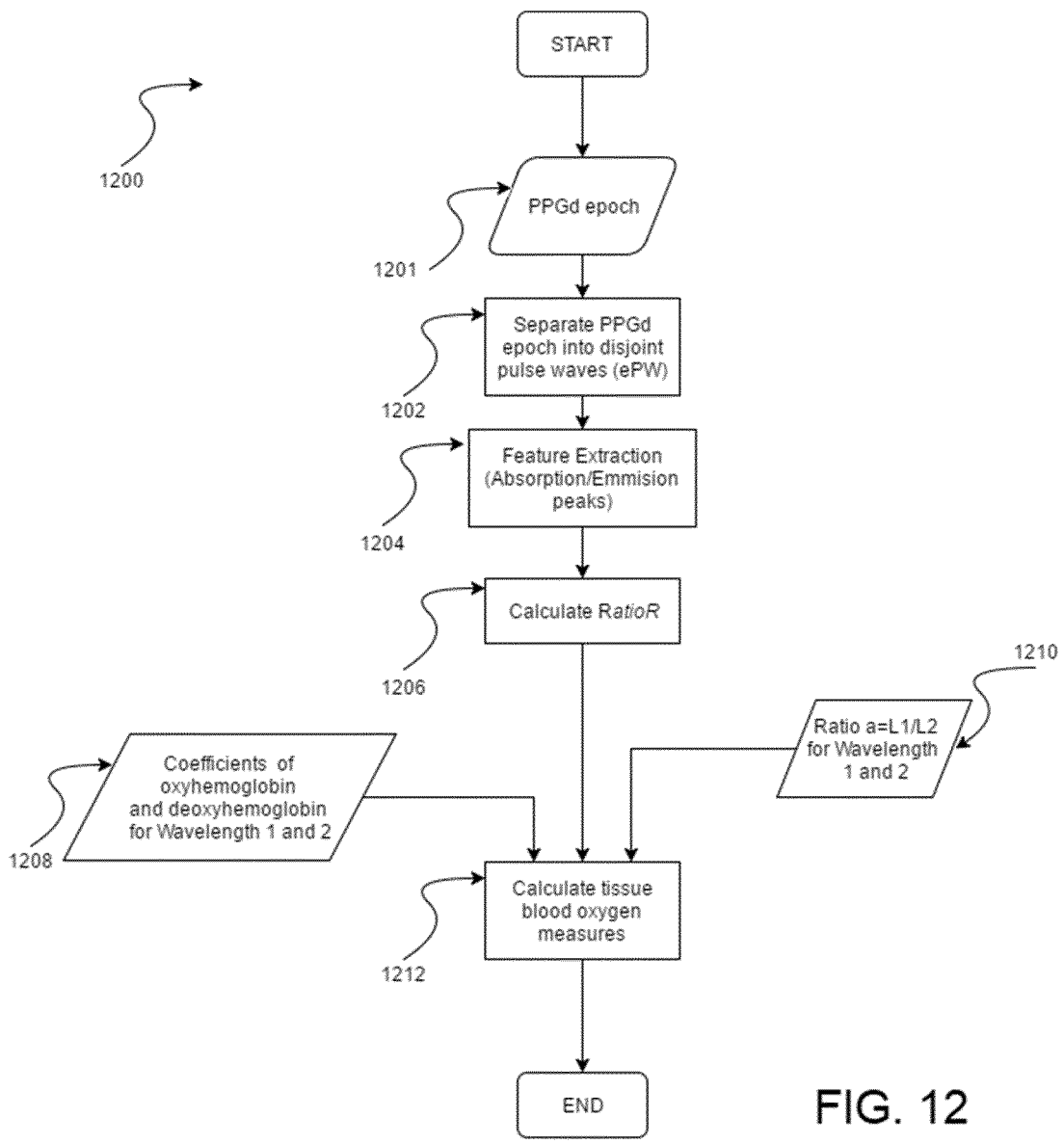
FIG. 12 schematically illustrates a flow chart of a method for calculating blood oxygen level according to an example.

FIG. 12 depicts a block diagram 1200 of a method for calculating the tissue Blood Oxygen Level (SpO2) from PPG readings.

The PPGd signal may be used as the basis for extracting meaningful measures. The emission (f2) and absorption (f3) peaks may be detected as described before in blocks 904 and 906, respectively. Then, in block 1201, the PPGd signal calculated according to any of the disclosed examples may be provided and the epochs of the PPGd may be segmented, in block 1202, into disjoint pulse waves which may be used to calculate, in block 1204, the latency, i.e. the amplitude, of emission and absorption peaks.

The user skin may, in an example, be illuminated with at least two different wavelengths e.g. Green light and IR radiation. The use of the at least two different wavelengths penetrating and then exiting the user tissue enables obtaining different absorption with distinct extinction coefficients. Light extinction coefficients of blood components, i.e. oxyhemoglobin (HbO) and deoxyhemoglobin (Hb) may be calculated from extinction coefficients as a function of wavelength measurements. Such light extinction coefficients are unique for each tissue impinging light wavelength.

The method 1200 for calculating the tissue blood oxygen level (SpO2) may further comprise calculating the RatioR, in block 1206, from the absorption and emission peaks of the PPGd signal. RatioR may be calculated by:

$$RatioR = \frac{\frac{\text{emission peak (wave1)} - \text{absorption peak (wave 1)}}{\text{absorption peak (wave 1)}}}{\frac{\text{emission peak (wave2)} - \text{absorption peak (wave 2)}}{\text{absorption peak (wave 2)}}}$$

Then, in block 1208, the extinction coefficients of oxyhemoglobin and deoxyhemoglobin may i.e. HbO1, HbO2 and Hb1, Hb2, of impinging first wavelength $\lambda 1$ and second wavelength $\lambda 2$, respectively, may be calculated. In an example, the first wavelength may correspond to green light and the second wavelength may be IR.

In block 1210, the unique wave propagation calibration coefficient $\alpha$ may be calculated according to predefined light propagation models accounting for different absorption and scattering of first and second wavelengths $\lambda 1$, $\lambda 2$ resulting to a difference of light propagation path length (L1, L2) within the illuminated tissue. Therefore, a may be calculated as:

$$\alpha = \frac{L_1}{L_2}$$

Then, in block 1212, the value of $SpO_2$ may be calculated by the following formula:

$$SpO_2 = \frac{Hb_1 - Hb_2 aR}{(HbO_2 - Hb_2)aR + (HbO_1 - Hb_1)} \times 100$$

In an alternative example, the Perfusion Index $PI_{PPG}$ of each signal epoch may be used to calculate the RatioR for the two wavelengths by dividing $PI_{PPG}$(wave1)/$PI_{PPG}$(wave2).

However, a single measurement of a biomarker cannot allow a precise determination of user health status. In an example, the system according to any of the disclosed examples used to implement any of the disclosed methods, may comprise a Personal Health Record (PHR) e.g. on the mobile device, thereby enabling short-term i.e. previous day, and/or long-term, i.e. previous week and month, comparative/contrasting vital signs monitoring.

The Cardiac Output (CO) may be calculated as the reciprocal ratio of the systolic and diastolic area of the PPGd pulse signals. The systolic area, in a pulse, is defined as the area under the curve bounded by the beginning of pulse and the dicrotic notch, whereas the diastolic area is bounded by the dicrotic notch and the end (absorption peak) of the pulse.

The Blood Flow Volume (BFV) is the volume of the blood measured considering a specific PTT, physiological parameters of a human body, and measurement position, where according to one example the device may be positioned on the posterior side of the wrist of a subject.

The Respiration Rate (RR) may be calculated using band pass filtering on Fast Fourier Transform (FFT) peak detection over noisy quasi-periodic signals selecting, according to one example, the dominant or most important frequency prior to the cardiac frequency.

The Heart Rate Variability (HRV) may be calculated by jointly measuring the interval time between emission, absorption and dicrotic notch/incisura peaks, according to one example the SD (standard deviation) and RMSSD (root mean square of successive differences of beat to beat intervals in time domain).

The Arterial Stiffness (AS, ASI), an independent screening measure for cardiovascular risk, related to aging and elastic properties of the arteries shows the contribution of wave reflection to systolic arterial pressure, and according to one example may be approximated by the ratio of the maximum peak to the minimum peak of the second derivative.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow. If reference signs related to drawings are placed in parentheses in a claim, they are solely for attempting to increase the intelligibility of the claim, and shall not be construed as limiting the scope of the claim.

The invention claimed is:

1. A timekeeping device configured to be worn by a user, the timekeeping device comprising:
   a body;
   a back case coupled to the body, the back case comprising:
   a casing having a bottom wall and a side wall defining an inner space;
   a plurality of openings provided at the bottom wall of the casing; and
   an optoelectronic circuit board disposed in the inner space of the casing, the optoelectronic circuit board comprising:
   a plurality of radiation sources arranged in selected ones of the plurality of openings provided at the bottom wall of the casing for illuminating the user's skin with radiation when the timekeeping device is worn by the user, each of the plurality of radiation sources having a different radiation emission wavelength to obtain a different degree of penetration into the user's skin; and
   at least one radiation detector for detecting a reflected radiation signal exiting from the user's skin as a result of the radiation illuminated on the user's skin by the plurality of radiation sources, and for transforming the reflected radiation signal into a processable signal, the at least one radiation detector being arranged in one of the plurality of openings other than the selected openings of the plurality of openings in which the plurality of radiation sources are arranged; and
   a band coupled to the body for mounting the timekeeping device around a wrist of the user so that the back case is in contact with the user's skin, the band comprising:
   a flexible layer having adjusting elements for adjusting the band to the user's wrist;
   coupling elements for coupling the flexible layer to the body of the timekeeping device;
   a buckle coupled to an end of the flexible layer, the buckle having a frame and a pivoting prong coupled to the frame for selective engagement with the flexible layer adjusting elements; and
   a tightening mechanism arranged in the frame of the buckle for obtaining a predefined adjustment of the band around the user's wrist to thereby increase the contact of the back case with the user's skin during illumination of the user's skin with the radiation by the plurality of radiation sources and detection of the reflected radiation signal by the at least one radiation detector, the tightening mechanism comprising a ratchet gear having locking teeth arranged at a periphery of the ratchet gear over a predetermined angular range, a pivoting strut configured for selective engagement with the locking teeth to place the tightening mechanism in a locked state, and a mechanism for pivoting the pivoting strut to disengage from the locking teeth to place the tightening mechanism in an unlocked state.

2. The timekeeping device according to claim 1, further comprising radiation guiding elements for guiding the radiation illuminated on the user's skin and for guiding the reflected radiation signal exiting from the user's skin.

3. The timekeeping device according to claim 2, wherein the radiation guiding elements comprise a first set of radiation guiding elements arranged between the at least one radiation detector and the user's skin, and a second set of radiation guiding elements arranged between the respective plurality of radiation sources and the user's skin.

4. The timekeeping device according to claim 1, wherein the optoelectronic circuit board further comprises:
   a control module for initiating and controlling data acquisition parameters;

a communication module for managing communications with an external mobile device;

an analogue to digital front end module for managing conversion of an analogue signal received by the at least one radiation detector to a digital signal and for controlling the plurality of radiation sources; and a power module including at least two voltage regulators for stabilizing voltages of the optoelectronic circuit board modules.

5. The timekeeping device according to claim 1, wherein the back case is configured to replace an existing removable back case of a timekeeping device.

6. The timekeeping device according to claim 1, wherein the back case is configured to be coupled to an existing back case of a timekeeping device.

7. The timekeeping device according to claim 1, wherein the timekeeping device is a wristwatch.

8. The timekeeping device according to claim 1, wherein the band further comprises a solid plate arranged below the flexible layer for ensuring a proper counterforce when the band is adjusted to the user's wrist.

9. A system for non-invasive measurements of biomarkers, the system comprising:

a timekeeping device configured to be worn by a user;

a back case coupled to a body of the timekeeping device, the back case including a casing having a bottom wall and a side wall defining an inner space, a plurality of openings provided at the bottom wall, and an optoelectronic circuit board disposed in the inner space, the optoelectronic circuit board comprising:

a plurality of radiation sources arranged in selected ones of the plurality of openings provided at the bottom wall of the casing for illuminating radiation on the user's skin when the timekeeping device is worn by the user, each of the plurality of radiation sources having a different radiation emission wavelength to obtain a different degree of penetration into the user's skin; and at least one radiation detector for detecting a reflected radiation signal exiting from the user's skin as a result of the radiation illuminated on the user's skin by the plurality of radiation sources and for generating a corresponding photoplethysmogram (PPG) signal, the at least one radiation detector being arranged in one of the plurality of openings other than the selected openings of the plurality of openings in which the plurality of radiation sources are arranged;

a band coupled to the body of the timekeeping device for mounting the timekeeping device around a wrist of the user so that the back case is in contact with the user's skin, the band comprising:

a flexible layer having adjusting elements for adjusting the band to the user's wrist;

coupling elements for coupling the flexible layer to the body of the timekeeping device;

a buckle coupled to an end of the flexible layer, the buckle having a frame and a pivoting prong coupled to the frame for selective engagement with the flexible layer adjusting elements; and a tightening mechanism arranged in the frame of the buckle for obtaining a predefined adjustment of the band around the user's wrist to thereby increase the contact of the back case with the user's skin during illumination of the user's skin with the radiation by the plurality of radiation sources and detection of the reflected radiation signal by the at least one radiation detector, the tightening mechanism comprising a ratchet gear having locking teeth arranged at a periphery of the ratchet gear over a predetermined angular range, a pivoting strut configured for selective engagement with the locking teeth to place the tightening mechanism in a locked state, and a mechanism for pivoting the pivoting strut to disengage from the locking teeth to place the tightening mechanism in an unlocked state;

means for extracting epochs from the PPG signal generated by the at least one radiation detector;

means for identifying pulses of the extracted epochs; and means for filtering the identified pulses until each pulse is within a predetermined reliability range.

10. The system according to claim 9, wherein each of the plurality of radiation sources is configured to illuminate the user's skin with the different radiation emission wavelength until a maximum gain of illuminating the skin is reached, wherein each of the different radiation emission wavelength is a predefined wavelength.

11. The system according to claim 10, wherein the predefined wavelength comprises a wavelength of 916-960 nm; and further comprising means for assessing a signal-to-noise ratio (SNR) and for increasing an amplification gain of illuminating the skin.

12. The system according to claim 11, wherein the means for assessing is configured to assess the SNR and increase the amplification gain by illuminating the skin with the predefined wavelength of 510-522 nm if the SNR is out of a predefined range of values.

13. The system according to claim 12, wherein the means for assessing is configured to assess a quality of the PPG signal using one of a kurtosis and skewness method.

14. The system according to claim 9, further comprising means for calculating an artefact-free derived PPG signal (PPGd) having a plurality of epochs comprising pulses.

15. The system according to claim 14, further comprising means for extracting features from the calculated PPGd signal by separating the pulses of each epoch of the PPGd signal.

16. The system according to claim 15, further comprising means for (a) extracting a falling edge (ePW(i)) of each of the pulses, (b) discarding beginning and end tails of each ePW(i), (c) calculating a first derivative of each ePW(i), (d) finding zero crossings (zCx) of each ePW(i), (e) determining a location of the zero crossings (zCx), (f) retrieving all dicrotic notch and incisura positions, and (g) repeating (a)-(f) for all pulses of the PPGd signal.

17. The system according to claim 9, wherein the predetermined reliability range substantially corresponds to a predefined PPG signal template.

18. The system according to claim 9, wherein means for filtering the PPG signal includes means for rejecting non-ideal pulses.

19. The system according to claim 9, further comprising means for re-evaluating the PPG signal by comparing the PPG signal with previously stored values of PPG signals.

20. The system according to claim 9, wherein the band further comprises a solid plate arranged below the flexible layer for ensuring a proper counterforce when the band is adjusted to the user's wrist.

* * * * *